(12) United States Patent
Kim et al.

(10) Patent No.: US 8,993,975 B2
(45) Date of Patent: Mar. 31, 2015

(54) GAMMA RAY DETECTING APPARATUS AND METHOD FOR DETECTING GAMMA RAY USING THE SAME

(75) Inventors: Chan-Hyeong Kim, Seoul (KR); Jin-Hyung Park, Seoul (KR); Hee Seo, Gyeonggi-do (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 0 days.

(21) Appl. No.: 14/111,103
(22) PCT Filed: Feb. 2, 2012
(86) PCT No.: PCT/KR2012/000809
§ 371 (c)(1),
(2), (4) Date: Oct. 10, 2013
(87) PCT Pub. No.: WO2012/141420
PCT Pub. Date: Oct. 18, 2012

(65) Prior Publication Data
US 2014/0021362 A1   Jan. 23, 2014

(30) Foreign Application Priority Data
Apr. 11, 2011   (KR) .......................... 10-2011-0033085

(51) Int. Cl.
| | |
|---|---|
| *G01T 1/20* | (2006.01) |
| *G01T 1/28* | (2006.01) |
| *G01T 1/29* | (2006.01) |
| *A61B 6/03* | (2006.01) |
| *A61B 6/00* | (2006.01) |

(52) U.S. Cl.
CPC ................ *G01T 1/2006* (2013.01); *G01T 1/28* (2013.01); *G01T 1/29* (2013.01); *A61B 6/037* (2013.01); *A61B 6/508* (2013.01)
USPC ...................... 250/370.01; 250/394

(58) Field of Classification Search
CPC ........................................... G01T 1/20
USPC ............................... 250/370.01, 394
See application file for complete search history.

(56) References Cited

U.S. PATENT DOCUMENTS 8,084,741 B2 * 12/2011 Gagnon et al. ............... 250/362

FOREIGN PATENT DOCUMENTS

| JP | 2000-292380 A | 10/2000 |
|---|---|---|
| JP | 2006-266996 A | 10/2006 |
| JP | 2007-333425 A | 12/2007 |
| KR | 1020060127087 A | 12/2006 |

OTHER PUBLICATIONS

International Search Report mailed Sep. 26, 2012; PCT/KR2012/000809.

* cited by examiner

*Primary Examiner* — David Porta
*Assistant Examiner* — Faye Boosalis
(74) *Attorney, Agent, or Firm* — Ladas & Parry LLP

(57) ABSTRACT

There are provided a gamma ray detecting apparatus, including: a secondary electron emitter causing a Compton scattering reaction with an incident gamma ray to emit secondary electrons in a progress direction of the gamma ray; a first radiation detector provided to be opposed to the secondary electron emitter with respect to an emission progress direction of the secondary electrons and detecting the position and transfer energy of the secondary electron; a second radiation detector provided to be opposed to the first radiation detector with respect to the emission progress direction of the secondary electron and detecting the position and the transfer energy of the secondary electron passing through the first radiation detector; a third radiation detector provided to be opposed to the second radiation detector with respect to the emission progress direction of the secondary electron and detecting residual energy of the secondary electron by absorbing the secondary electron passing through the second radiation detector; and a data processor having a coincidence circuit judging whether the secondary electrons simultaneously react in the first to third radiation detectors, and the data processor back traces trajectories of the secondary electrons detected by the first and second radiation detectors to detect the position of a ray source of the gamma ray, and a gamma ray detecting method.

14 Claims, 4 Drawing Sheets

GAMMA RAY DETECTING APPARATUS AND METHOD FOR DETECTING GAMMA RAY USING THE SAME

BACKGROUND OF THE INVENTION

1. Field of the Invention

The present invention relates to a gamma ray detecting apparatus and a method for detecting a gamma ray using the same, and more particularly, to a gamma ray detecting apparatus and a method of detecting a gamma ray using the same capable of imaging location and distribution of ray sources of the gamma ray by reversely tracking a trace of a secondary electron generated in Compton scattering reaction of a gamma ray emitted from a gamma ray source or nuclear reaction.

2. Description of the Related Art

In general, in cancer treatment using a radiation, it is important to remove a cancer cell and prevent neighboring normal tissues from being damaged by locally transferring radiation energy to only a cancer tissue. Since a photon beam or an electron beam is used in conventional radiation treatment, it is difficult to limitedly apply a beam amount to the cancer tissue.

Meanwhile, in the case of cancer treatment using protons, the beam amount can concentrate on a desired portion and the damage of the neighboring normal tissues can be minimized due to a peculiar energy transfer characteristic called Bragg Peak.

However, up to now, a technology that accurately decides a Bragg Peak location in a patient's body in real time during treatment has not yet be provided, and as a result, a technology has held the limelight, which infers the Bragg Peak location through a distribution of a prompt gamma ray generated by a reaction between the protons and a target material.

In order to infer the Bragg Peak location, a gamma ray emission imaging device constituted by a focusing device and a position sensitive radiation detector is used and in the gamma ray emission imaging device, when the gamma ray emitted from a radiation source passes through the focusing device and thereafter, reacts in the position sensitive radiation detector, data generated at that time is acquired to image a distribution of the radiation source.

However, the existing gamma ray emission imaging device has various problems. In the existing gamma ray emission imaging device, since most gamma rays are removed by the focusing device, it is difficult to acquire high image sensitivity. Further, since the gamma ray is high in transmittance and low in reaction probability, it is difficult to expect high image sensitivity when the gamma ray is directly detected. In the conventional gamma ray emission imaging device, since image resolution and image sensitivity depend on a structure of the focusing device and have a conflicting characteristic to each other, there is a limit that the image resolution or image sensitivity cannot be independently improved.

Moreover, when energy of the gamma ray increases, the performance of the focusing device is rapidly degraded, and as a result, the image resolution is degraded. Therefore, the convention imaging device of the above scheme can be substantially applied to only a gamma ray of 1 MeV or less.

Further, since a target should be scanned while placing a measurement system measuring the gamma ray circularly or rotating the measurement system in order to acquire an image of the ray source emitting the gamma ray in a 3 dimension, there is a limit in minimizing the device and manufacturing cost is also high.

SUMMARY OF THE INVENTION

An aspect of the present invention provides a gamma ray detecting apparatus and a method for detecting a gamma ray using the same with which it is possible to indirectly detect location and distribution of a gamma ray source by using a secondary electron generated after a gamma ray is primarily converted into an electron, when a ray source of the gamma ray is detected.

An aspect of the present invention also provides a gamma ray detecting apparatus and a method for detecting a gamma ray using the same with which it is possible to enhance image resolution for a gamma ray source emitting a high-energy gamma ray and improve measurement efficiency.

An aspect of the present invention also provides a gamma ray detecting apparatus and a method for detecting a gamma ray using the same with which it is possible to three-dimensionally acquire location and distribution of a gamma ray source at a fixed position.

An aspect of the present invention also provides a gamma ray detecting apparatus and a method for detecting a gamma ray using the same with which it is possible to achieve a small size and a light weight of a device for acquiring an image of a gamma ray source.

According to an aspect of the present invention, there is provided a gamma ray detecting apparatus, including: a secondary electron emitter causing a Compton scattering reaction with an incident gamma ray to emit secondary electrons in a progress direction of the gamma ray; a first radiation detector provided to be opposed to the secondary electron emitter with respect to an emission progress direction of the secondary electrons and detecting the position and transfer energy of the secondary electron; a second radiation detector provided to be opposed to the first radiation detector with respect to the emission progress direction of the secondary electron and detecting the position and the transfer energy of the secondary electron passing through the first radiation detector; a third radiation detector provided to be opposed to the second radiation detector with respect to the emission progress direction of the secondary electron and detecting residual energy of the secondary electron by absorbing the secondary electron passing through the second radiation detector; and a data processor having a coincidence circuit judging whether the secondary electrons simultaneously react in the first to third radiation detectors, and the data processor back or reversely traces trajectories of the secondary electrons detected by the first and second radiation detectors to detect the position of a ray source of the gamma ray.

The first radiation detector or the second radiation detector may detect the positions of the plurality of secondary electrons, and the data processor may detect the ray source of the gamma ray from a cross point of lines connecting the positions of the secondary electrons.

The secondary electron emitter may be made of any one of liquefied helium, beryllium, and distilled water so that the secondary electron is emitted from the secondary electron emitter while maintaining a linear trajectory.

The first radiation detector or the second radiation detector may be made of a material having a low atomic number or a low density so as for the secondary electron emitted from the secondary electron emitter to maintain the linear trajectory while passing through the first radiation detector or the second radiation detector.

The first radiation detector or the second radiation detector may be formed in a double-sided silicon strip type.

An interval between the first and second radiation detectors may be larger than an interval between the second and third radiation detectors. That is, the interval between the first and second radiation detectors should be sufficiently large and the interval between the second and third radiation detectors is preferably minimized.

A thickness of the third radiation detector may be larger than a thickness of the first radiation detector or the second radiation detector. The third radiation detector is preferably sufficiently thick and the reason is that all secondary electrons and x-rays generated while the secondary electron is absorbed in the third radiation detector need to be absorbed of itself in order to accurately decide energy of the secondary electron that passes through the second radiation detector.

The gamma ray detecting apparatus may include an energy selector that sums up the energy of the secondary electrons detected by the first to third radiation detectors and judges whether the summed energy is included in a set reference energy range. It is possible to judge whether data detected by the selector may judge is effective data to acquire the position of the gamma ray source as a 3D image.

According to another aspect of the present invention, there is provided a gamma ray detecting method using the gamma ray detecting apparatus, including: (a) causing a Compton scattering reaction with the gamma ray incident in the secondary electron emitter and emitting the secondary electron in the same direction as a progress direction of the gamma ray; (b) detecting the position and transfer energy of the secondary electron at the time when the secondary electron passes through the first radiation detector; (c) detecting the position and transfer energy of the secondary electron at the time when the secondary electron passes through the second radiation detector; (d) detecting residual energy of the secondary electron at the time when the secondary electron is absorbed in the third radiation detector; (e) detecting data of the secondary electron detected simultaneously detected by the first to third radiation detectors by using the data processor; (f) detecting the position of a ray source of the gamma ray by back-tracing (or reversely tracing) a trajectory of the secondary electron detected by the first and second radiation detectors; and (g) acquiring as an image data included in a reference energy range in which the sum of the energy of the secondary electron detected by the first to third radiation detectors.

Step (b) may include measuring a position Pa1 and Pb1 where the plurality of secondary electrons passes through the first radiation detector and energy Ea1 and energy Eb1 transferred by the secondary electron at the time when the plurality of secondary electrons passes through the position Pa1 and the position Pb1, and step (c) may include measuring a position Pa2 and a position Pb2 where the secondary electron passing through the first radiation detector passes through the second radiation detector and energy Ea2 and energy Eb2 transferred by the secondary electron at the time when the secondary electron passes through the positions Pa2 and Pb2.

In step (f), a trajectory connecting the measured positions Pa1 and Pa2 and a trajectory connecting the positions Pb1 and Pb2 are back-projected to judge a point where both trajectories cross each other as the position of the ray source of the gamma ray.

In step (e), the data of the secondary electron simultaneously detected by the first to third radiation detectors may be selected by using a coincidence circuit. The reason is that a very thin detector is used as the first and second radiation detectors, a non-charged particle very rarely reacts with both detectors react with each other while two detecting and at the same time, a case in which a coincidence is satisfied is by a charged particle.

In step (e), the data included in a reference energy range (or sum energy windows) in which the sum of the energy of the secondary electron detected by the first to third radiation detectors is selected.

In step (e), the data included in respective reference energy ranges (or energy windows) in which the energy of the secondary electron transferred to the first and second radiation detectors may be selected. Since the data included in the reference energy range is selected as above, data included in base energy is regarded as an effective reaction and remnant may be effectively removed.

As described above, the gamma ray detecting apparatus and the gamma ray detecting method according to the present invention, since the position of a gamma ray source is indirectly detected by back-tracing an emission trajectory of a secondary electron generated in reaction with a gamma ray, detection efficiency can be increased and image resolution for a high-energy gamma ray source can be improved.

The gamma ray detecting apparatus and the gamma ray detecting method according to the present invention can image the position and the distribution of the gamma ray source in 3D at a fixed position and user convenience to use an apparatus can be increased by decreasing the size and weight of an apparatus for detecting the gamma ray source.

Since the gamma ray detecting apparatus and the gamma ray detecting method according to the present invention adopts an energy selector, the gamma ray detecting apparatus and the gamma ray detecting method can be minimize noise.

The gamma ray detecting apparatus and the gamma ray detecting method according to the present invention can be applied to imaging a radioactive isotope emitting a gamma ray having high energy.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
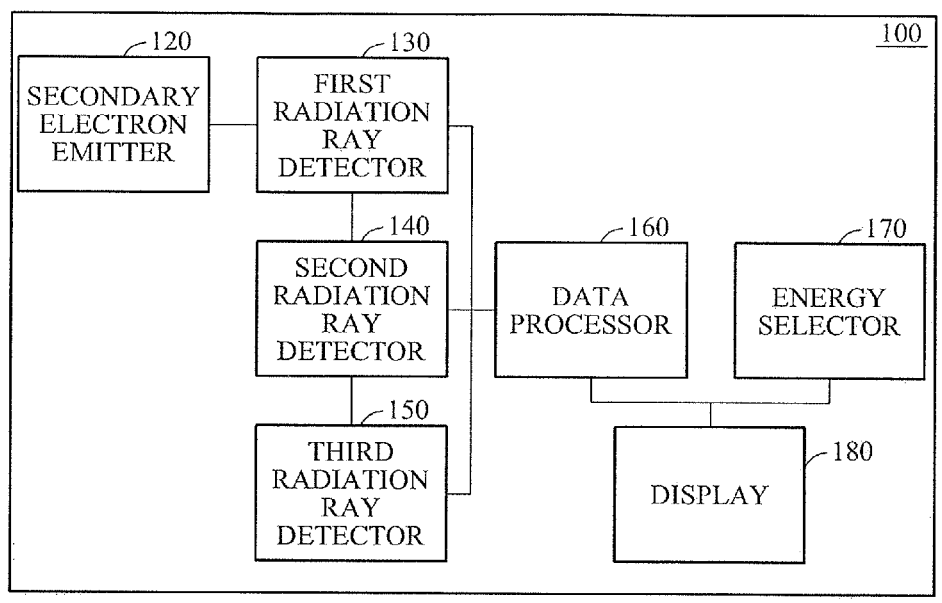
FIG. 1 is a block diagram schematically illustrating a gamma ray detecting apparatus according to an exemplary embodiment of the present invention.

Hereinafter, exemplary embodiments of the present invention will be described in detail with reference to the accompanying drawings. However, the present invention is not limited or restricted to the exemplary embodiments. The same reference numerals denoted in the drawings are assigned to the same components.

Figure 2:
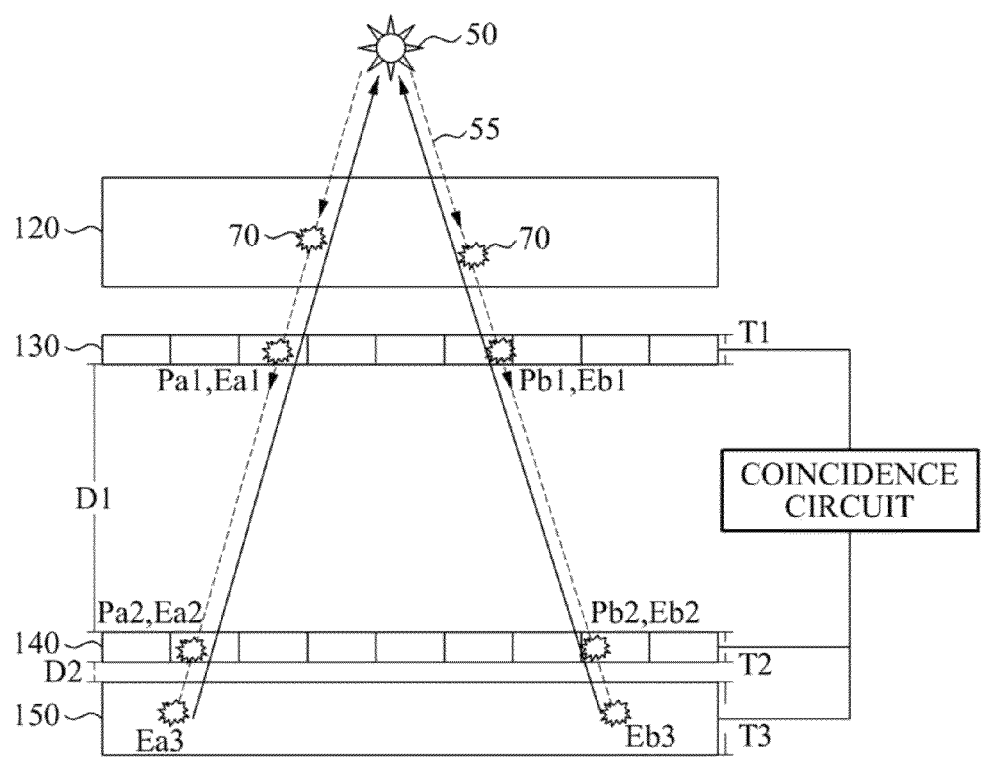
FIG. 2 is a view schematically illustrating a gamma ray detecting apparatus according to an exemplary embodiment of the present invention.
Figure 3:
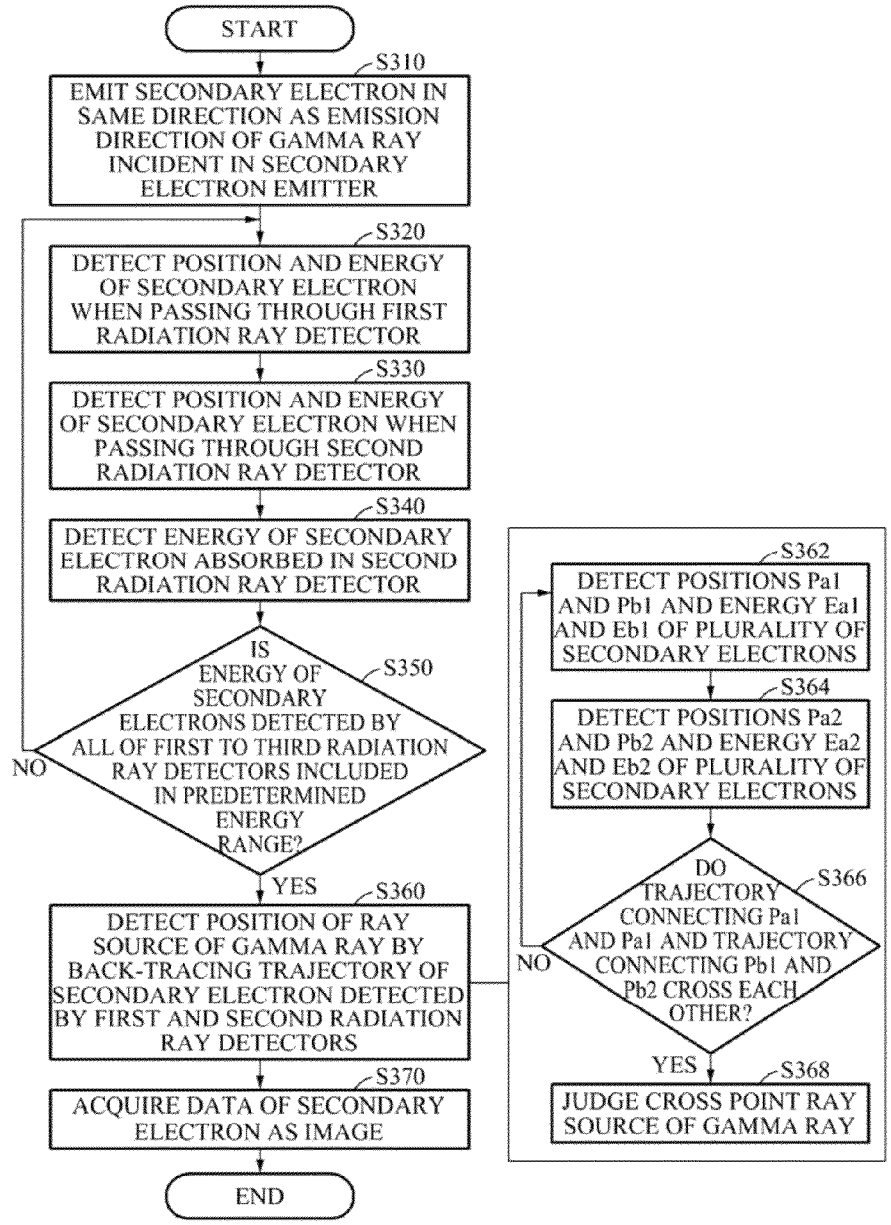
FIG. 3 is a flowchart describing a method of detecting a gamma ray according to an exemplary embodiment of the present invention.
Figure 4:
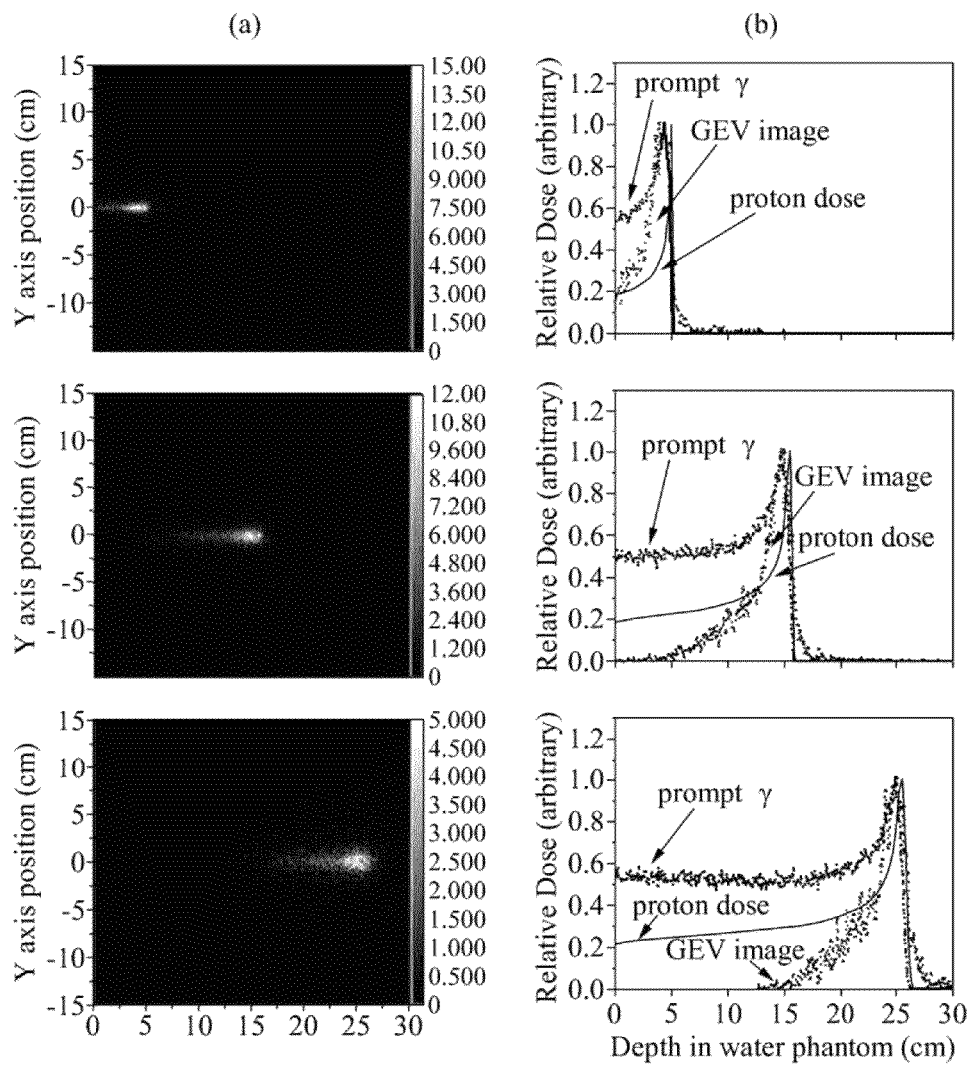
FIG. 4 is a view illustrating a result acquired by experiment a beam path of proton beam by using a gamma detecting apparatus according to an exemplary embodiment of the present invention.

FIG. 1 is a block diagram schematically illustrating a gamma ray detecting apparatus according to an exemplary embodiment of the present invention, FIG. 2 is a view schematically illustrating a gamma ray detecting apparatus according to an exemplary embodiment of the present invention, FIG. 3 is a flowchart describing a method of detecting a gamma ray according to an exemplary embodiment of the present invention, and FIG. 4 is a view illustrating a result acquired by experiment a beam path of proton beam by using a gamma detecting apparatus according to an exemplary embodiment of the present invention.

Referring to FIGS. 1 and 2, a gamma ray detecting apparatus according to an exemplary embodiment of the present invention may include various devices capable of detecting a location of a ray source 50 of a gamma ray 55, and a display device 180 displaying the location and distribution of the ray source 50 of the gamma ray 55 detected from each device with an image.

When the various devices capable of detecting the location of the gamma ray source 50 of the gamma ray 55 is described in more detail, the gamma ray 55 emitted from the gamma ray source 50 passes through a secondary electron emitter 120. The secondary electron emitter 120 is formed by a material which reacts with the incident gamma ray 55 to generate secondary electrons 70, and the gamma ray 55 generated from the ray source 50 of the gamma ray 55 causes a Compton scattering reaction to generate the secondary electrons 70.

The secondary electron emitter 120 may be made of a material having a low atomic number which relatively causes the Compton scattering reaction well so that the secondary electrons 70 are more efficiently generated by the gamma ray 55 having high energy. Further, the secondary electron emitter 120 may be made of a material having a low atomic number and low density so that the generated secondary electrons 70 may be linearly emitted with little change of a trace in the secondary electron emitter 120. For example, the secondary electron emitter 120 may be made of liquid helium, beryllium, distilled water, or the like, and of course, the secondary electron emitter 120 may be replaced with another material which may generate the secondary electrons 70 in the reaction with the gamma ray 55 other than the described materials.

Meanwhile, the secondary electrons 70 emitted from the secondary electron emitter 120 pass through a first radiation detector 130 which is provided to face the secondary electron emitter 120 in an emission progress direction of the secondary electrons 70 and detects the location of the secondary electrons 70 and transfer energy. Here, the transfer energy is energy of the secondary electrons 70 transferred to the first radiation detector 130.

The first radiation detector 130 primarily determines a trace of the secondary electrons 70 emitted from the secondary electron emitter 120, has a very small thickness for minimizing a trace change of the secondary electrons 70, and may be made of a material having a low atomic number and low density. That is, the first radiation detector 130 is made of the material having a low atomic number and low density, and as a result, the trace of the secondary electrons 70 may maximally maintain a straight line while or after passing through the first radiation detector 130 and a change in linear trace may be minimized.

Meanwhile, the secondary electrons 70 passing through the first radiation detector 130 pass through a second radiation detector 140. The second radiation detector 140 may be provided to face the first radiation detector 130 in the emission progress direction of the secondary electrons 70, and detects the location and transfer energy of the secondary electrons 70 passing through the first radiation detector 130.

The second radiation detector 140 has also a small thickness so as to minimize a change in linear trace while the secondary electrons 70 emitted from the first radiation detector 130 pass through a second radiation detector 140 and may be made of a material having a low atomic number and low density. The first and second radiation detectors 130 and 140 may be made of the same material, but may be made of different materials according to a condition of the invention. For example, the first radiation detector 130 and the second radiation detector 140 may be formed by a double-sided silicon stripe type.

The secondary electrons 70 emitted from the second radiation detector 140 are absorbed in a third radiation detector 150. That is, the secondary electrons 70 pass through both the first radiation detector 130 and the second radiation detector 140, and then are finally completely absorbed in the first radiation detector 130 and the second radiation detector 140 and stops. The third radiation detector 150 fully absorbs residue energy of the secondary electrons 70 emitted from the second radiation detector 140, and as a result, the secondary electrons 70 stop in the third radiation detector 150 and the absorbed residue energy is measured, and a total energy selector may be applied below.

Here, the first radiation detector 130 and the second radiation detector 140 detect the location and the transfer energy of the secondary electrons 70, while the third radiation detector 150 detects only the residue energy of the secondary electrons 70.

In this case, a distance D1 between the first and second radiation detectors 130 and 140 may be larger than a distance D2 between the second and third radiation detectors 140 and 150. As illustrated in FIG. 2, the distance D1 between the first and second radiation detectors 130 and 140 may be separated by a sufficient distance so as to more accurately determine the linear trace of the secondary electrons 70 by reversely tracking the location of the secondary electrons 70 detected in the first and second radiation detectors 130 and 140.

On the contrary, in order that the secondary electrons 70 passing through the second radiation detector 140 is all incident to the third radiation detector 150 to be completely absorbed, the distance D2 between the second radiation detector 140 and the third radiation detector 150 may be minimized or smaller than the distance D1 between the first radiation detector 130 and the second radiation detector 140. As such, in order to more accurately measure the linear trace of the secondary electrons 70, the distance D1 between the first and second radiation detectors 130 and 140 needs to be sufficiently increased, and in order to efficiently measure or detect the secondary electron passing through the second radiation detector 140, the distance D2 between the second and third radiation detectors 140 and 150 may be minimized.

Further, a thickness T3 of the third radiation detector 150 may be larger than thicknesses T1 and T2 of the first and second radiation detectors 130 and 140. As described above, the third radiation detector 150 serves to determine energy of the secondary electrons 70 emitted from the second radiation detector 140. While the secondary electrons 70 are finally completely absorbed in the third radiation detector 150, another secondary electron and an X-ray are generated. Accordingly, in order to more accurately determine the energy of the secondary electrons 70 emitted from the second radiation detector 140, the thickness T3 of the third radiation detector 150 is sufficiently increased so as to absorb all secondary radiation generated while the secondary electrons 70 are absorbed in the third radiation detector 150 by themselves.

The thicknesses T1 and T2 of the first and second radiation detectors 130 and 140 may be formed as thinly as possible in order to minimize an effect on the trace of the secondary electrons 70. In this case, the thicknesses T1 and T2 of the first and second radiation detectors 130 and 140 may be the same as each other like the exemplary embodiment of the present invention, but of course, may be different from each other.

Meanwhile, the gamma ray detecting apparatus 100 may include a data processor 160 having a coincidence counter circuit determining whether the secondary electrons 70 react in all of the first to third radiation detectors 130, 140, and 150 in order to track the location of the gamma ray source 50.

The data processor 160 acquires data of the secondary electrons 70 which coincidentally react by applying the coincidence counter circuit to the first to third radiation detectors 130, 140, and 150 to decrease a background or increase a signal to noise ratio.

Further, the data processor 160 reversely tracks the trace of the secondary electrons 70 detected in the first and second radiation detectors 130 and 140 to detect the location of the ray source 50 of the gamma ray 55. That is, the data processor 160 connect locations of a plurality of secondary electrons 70 detected in the first and second radiation detectors 130 and 140 with lines to detect locations where the lines cross each other. Cross points of the detected lines may be assumed as 3-dimensional locations of the gamma ray source 50, and a plurality of lines is acquired, thereby 3-dimensionally imaging the distribution of the gamma ray source 50. In other words, when the trace of the plurality of secondary electrons 70 is reversely projected, the location of the gamma ray source 50 may be 3-dimensionally imaged. As a result, the location of the gamma ray source 50 may be 3-dimensionally detected without moving the gamma ray detecting apparatus 100 according to the exemplary embodiment of the present invention. Accordingly, convenience of a user may be improved by decreasing the apparatus in size and weight.

Meanwhile, the gamma ray detecting apparatus 100 according to the exemplary embodiment of the present invention may further include an energy selector 170 which combines the energy of the secondary electrons 70 detected from the first to third radiation detectors 130, 140, and 150 and determines whether the combined energy is included within a set reference energy range or sum energy windows.

The energy selector 170 may calculate total energy by combining the energy of the secondary electrons 70 detected from the first to third radiation detectors 130, 140, and 150 in the data processor 160 and determine whether the calculated total energy is included in a predetermined energy region. The predetermined energy region and range is an energy region and range of the gamma ray 55 emitted from the gamma ray source 50 to be imaged by the user, and the energy region may be changed according to a condition required in the invention.

When the total energy acquired by combining all the energy detected from the first to third radiation detectors 130, 140, and 150 in the energy selector 170 is included in the predetermined energy region, the data is determined as usable data, and may be used to track the location of the ray source 50 of the gamma ray 55. Further, the energy transferred to the three detectors 130 to 150 by the energy selector 170 may improve the signal to noise ratio and decrease the background. The reason is that although the data is data satisfying coincidence counting by the coincidence counter circuit in accordance with data processing, when the energy transferred to the detectors is not included in the predetermined energy region, it may not be considered as effective reaction. If the total energy of the secondary electrons 70 detected from the energy selector 170 is not included in the predetermined energy region, the data are all removed to decrease the background and increase the signal to noise ratio. The energy selector 170 is provided, and as a result, data in the case where charged particles having different weights like protons may be removed from the effective data.

Here, in order to selectively detect only the secondary electrons 70, separate independent energy selectors are used in the first and second radiation detectors 130 and 140, and additionally, an energy selector 170 for determining whether the total energy acquired by combining all the energy transferred to the three radiation detectors 130,140, and 150 is included in the predetermined energy region and range may be separately applied.

By the configuration, since the gamma ray source 50 is tracked by easily imaging the gamma ray source 50 emitting the high energy gamma ray 55 or distribution of nuclear reaction, detecting the location and the energy of the secondary electrons 70 generated from the secondary electron emitter 120, and reversely tracking the trace of the detected secondary electrons 70, the location of the gamma ray source 50 may be indirectly tracked and more accurately tracked with high efficiency.

Hereinafter, a method of measuring the gamma ray 55 according to an exemplary embodiment of the present invention will be described in more detail with reference to drawings.

Referring to FIG. 3, in the method of measuring the gamma ray 55 according to an exemplary embodiment of the present invention, the gamma ray 55 emitted from the gamma ray source 50 is incident to the secondary electron emitter 120, the gamma ray incident to the secondary electron emitter 120 causes a Compton scattering reaction, and the secondary electrons 70 may be emitted in the same direction as an incident direction of the gamma ray 55 (S310).

In this case, the gamma ray 55 emitted from the gamma ray source 50 may use the high energy gamma ray 55. As such, the reason of preferring the high energy gamma ray 55 is that as the energy of the gamma ray 55 is increased, most of initial energy of the gamma ray 55 is transferred to the secondary electrons 70, and most of the secondary electrons 70 receiving the energy of the gamma ray are emitted as it is in the same direction as a progress direction of the gamma ray 55. For example, maximum transfer energy transferred to the secondary electrons 70 is 66.2% in the case of a 1 MeV gamma ray, and about 97.5% in the case of a 10 MeV gamma ray.

As described above, the emitted secondary electrons 70 pass through the first radiation detector 130 and the location and the transfer energy of the secondary electrons 70 are detected when the secondary electrons 70 pass through the first radiation detector 130 (S320), and the location of the ray source 50 of the gamma ray 55 is detected by reversely tracking the trace of the secondary electrons 70 detected from the first and second radiation detectors 130 and 140 (S360).

Here, the position where the plurality of secondary electrons 70 pass through the first radiation detector 130 and the transfer energy at this time are set as two points, and if two points are referred to as positions Pa1 and Pb1 and the transfer energy at each position is referred to as Ea1 and Eb1, the positions of the plurality of secondary electrons and the transfer energy at each position may be detected (S362). Meanwhile, in a method of detecting a gamma ray according to the exemplary embodiment of the present invention, a case where the position and the energy of the secondary electrons 70 are calculated with respect to the two points is described as an example, but three or more points are set, and a position and transfer energy at each point may be detected.

The secondary electrons 70 passing through the first radiation detector 130 pass through the second radiation detector 140, and a position and transfer energy of the secondary electrons 70 when passing through the second radiation detector 140 may be detected (S330). Even in this case, like the detecting of the position and the energy of the secondary electrons 70 in the first radiation detector 130 described above, if a plurality of positions passing through the second radiation detector 140 are referred to as Pa2 and Pb2 and transfer energy at each position is referred to as Ea2 and Eb2, the positions of the plurality of secondary electrons and transfer energy at each position may be detected, respectively (S363).

As such, the positions Pa2 and Pb2 and the energy Ea2 and Eb2 are detected, and while the secondary electrons 70 passing through the second radiation detector 140 is completely absorbed in the third radiation detector 150, residue energy of the secondary electrons 70 may be detected (S340).

The position Pa1 and the position Pa2 of the secondary electrons 70 measured in the first and second radiation detectors 130 and 140 are connected to each other in a trace or a line, and further, the position Pb1 and the position Pb2 are connected to each other in a trace or a line. The cross points are tracked by reversely projecting each connected trace (S366), and it is determined that the gamma ray source 50 is positioned at the cross points of the lines by reversely tracking the trace of the secondary electrons 70(S368).

In this case, in the exemplary embodiment of the present invention, in order to 3-dimensionally determine the position of the gamma ray source 50, an example in which the trace of the two secondary electrons 70 is reversely tracked is described, but the trace reversely tracked by selecting the position of the plurality of secondary electrons 70 is collected at one point to determine the position of the gamma ray source 50.

In this case, it is determined whether a sum of the energy of the secondary electrons 70 detected from the first to third radiation detectors 130, 140, and 150 is included in the predetermined reference energy range or sum energy windows (S350), and an image is acquired by using only the data of the secondary electrons 70 included in the reference energy range (S370).

Further, it is determined whether the energy of the secondary electrons 70 transferred to the first radiation detector 130 and the second radiation detector 140 is included in the predetermined reference energy range, and only the data of the secondary electrons 70 included in the reference energy range may be selected.

In the process of detecting the data, only the data, in which the reaction is caused at the same time in all of the three detectors by applying the coincidence counter circuit to the three radiation detectors, are recorded. In this case, since very thin detectors are used as the first and second radiation detectors 130 and 140, a case where non-charged particles directly react with the two detectors at the same time is quire rare, and in the case of satisfying the coincidence counter, it is determined that nearly all are performed by charged particles.

Further, the total energy acquired by adding all the energy detected from the first to third radiation detectors 130, 140, and 150 is applied to the energy selector 170. The energy selector 170 means that even in the case of the data recorded by satisfying the coincidence counter in the data processor 160, only when the data is within the energy range set by the user, the data is considered as the effective reaction, and the remaining data is removed. As a result, a case where other charged particles react may be effectively removed.

Hereinafter, a result of the beam path of the proton beam is examined by the apparatus and the method to examine accuracies of the gamma ray detecting apparatus and the gamma ray detecting method according to the exemplary embodiments of the present invention.

FIG. 4 illustrates a photograph and a graph acquired by experimenting the beam path and the position of the proton beam in a water phantom while irradiating the proton beam having treatment energy to the water phantom by using the gamma ray detecting apparatus and the gamma ray detecting method according to the exemplary embodiments of the present invention. That is, the proton reacts with the water phantom to generate a prompt gamma ray and a distribution of the prompt gamma ray is imaged by using trajectory tracing and coincidence of secondary electrons, an energy selector, a ray back-projection technique, and the like. The energy of the proton beam used at that time is 80, 150, 200 MeV.

The experiment is performed by changing the size of the water phantom for each energy by considering a spreading degree of the proton beam. Herein, the water phantom may serve as the secondary electron emitter 120. The size of the water phantom is $2 \times 2 \times 30$ cm$^3$ (80 Mev proton beam), $3 \times 3 \times 30$ cm$^3$ (150 MeV proton beam), and $4 \times 4 \times 30$ cm$^3$ (200 MeV proton beam) with respect to respective proton beams.

Referring to FIG. 4, a top photograph and a top graph, a second photograph and a second graph, and a bottom photograph and a bottom graph illustrate cases in which 80 MeV proton beam, 150 MeV proton beam, and 200 MeV proton beam are irradiated to the water phantom, respectively.

Further, in FIG. 4, a left (a) photograph shows the image of the distribution of the prompt gamma ray acquired by using the gamma ray detecting apparatus and the gamma ray detecting method according to the exemplary embodiments of the present invention and a right (b) photograph shows a pixel value (see a GEV image) acquired along a central axis of the corresponding image, a generation distribution of the prompt gamma ray in the water phantom (see prompt γ), and a distribution of a proton beam amount (see proton dose).

Herein, the graph marked with "prompt γ" in FIG. 4(b) shows a distribution of the prompt gamma ray 55 generated by the proton beam and the graph marked with "GEV image" shows the pixel value of the image acquired by the gamma ray detecting apparatus 100 and the gamma ray detecting method of the present invention.

Referring to FIG. 4, it can be seen that the distribution of the prompt gamma ray 55 and data acquired by the gamma ray detecting apparatus 100 and the gamma ray detecting method of the present invention very accurately coincide with each other with an error of 1 mm or less. Therefore, it is possible to accurately infer the beam path of the proton beam in real time during the treatment or experiment using the proton beam.

The gamma ray detecting apparatus 100 and the gamma ray detecting method using the same described above may be applied to various fields such as nuclear medicine and molecular imaging for a medical purpose, an image device for a small animal, brain science, hydrography using a radiotracer, space physics, and the like, and when a high-energy gamma ray source is used, a more excellent image may be acquired. In particular, in a proton treatment facility, the gamma ray detecting apparatus 100 and the gamma ray detecting method using the same may be used in a device of deciding the beam path and position of the proton beam in real time during treatment or applied to a space gamma ray measuring and imaging apparatus for astrophysics such as a pulser or a supernova remnant research.

The specified matters and limited embodiments and drawings such as specific components in the embodiment of the present invention have been disclosed for illustrative purposes, but are not limited thereto, and those skilled in the art will appreciate that various modifications, additions and substitutions are possible from the disclosure in the art to which the present invention belongs. The spirit of the present invention is defined by the appended claims rather than by the description preceding them, and all changes and modifications that fall within metes and bounds of the claims, or equivalents of such metes and bounds are therefore intended to be embraced by the range of the spirit of the present invention.

The present invention can be applied to a medical field or a space gamma ray imaging field.

What is claimed is:

1. A gamma ray detecting apparatus, comprising:
    a secondary electron emitter causing a Compton scattering reaction with an incident gamma ray to emit secondary electrons in a progress direction of the gamma ray;
    a first radiation detector provided to be opposed to the secondary electron emitter with respect to an emission progress direction of the secondary electrons and detecting the position and transfer energy of the secondary electron;
    a second radiation detector provided to be opposed to the first radiation detector with respect to the emission progress direction of the secondary electron and detecting the position and the transfer energy of the secondary electron passing through the first radiation detector;
    a third radiation detector provided to be opposed to the second radiation detector with respect to the emission progress direction of the secondary electron and detecting residual energy of the secondary electron by absorbing the secondary electron passing through the second radiation detector; and
    a data processor having a coincidence circuit judging whether the secondary electrons simultaneously react in the first to third radiation detectors,
    wherein the data processor back traces trajectories of the secondary electrons detected by the first and second radiation detectors to detect the position of a ray source of the gamma ray.

2. The gamma ray detecting apparatus of claim 1, wherein:
    the first radiation detector or the second radiation detector detects the positions of the plurality of secondary electrons, and
    the data processor detects the ray source of the gamma ray from a cross point of lines connecting the positions of the secondary electrons.

3. The gamma ray detecting apparatus of claim 2, wherein:
    the secondary electron emitter is made of any one of liquefied helium, beryllium, and distilled water so that the secondary electron is emitted from the secondary electron emitter while maintaining a linear trajectory.

4. The gamma ray detecting apparatus of claim 3, wherein:
    the first radiation detector or the second radiation detector is made of a material having a low atomic number or a low density so as for the secondary electron emitted from the secondary electron emitter to maintain the linear trajectory while passing through the first radiation detector or the second radiation detector.

5. The gamma ray detecting apparatus of claim 4, wherein:
    the first radiation detector or the second radiation detector is formed in a double-sided silicon strip type.

6. The gamma ray detecting apparatus of claim 4, wherein:
    an interval between the first and second radiation detectors is larger than an interval between the second and third radiation detectors.

7. The gamma ray detecting apparatus of claim 6, wherein:
    a thickness of the third radiation detector is larger than a thickness of the first radiation detector or the second radiation detector.

8. The gamma ray detecting apparatus of claim 4, comprising:
    an energy selector that sums up the energy of the secondary electrons detected by the first to third radiation detectors and judges whether the summed energy is included in a set reference energy range.

9. A gamma ray detecting method using the gamma ray detecting apparatus of claim 1, the method comprising:
    (a) causing a Compton scattering reaction with the gamma ray incident in the secondary electron emitter and emitting the secondary electron in the same direction as a progress direction of the gamma ray;
    (b) detecting the position and transfer energy of the secondary electron at the time when the secondary electron passes through the first radiation detector;
    (c) detecting the position and transfer energy of the secondary electron at the time when the secondary electron passes through the second radiation detector;
    (d) detecting residual energy of the secondary electron at the time when the secondary electron is absorbed in the third radiation detector;
    (e) detecting data of the secondary electron detected simultaneously detected by the first to third radiation detectors by using the data processor;
    (f) detecting the position of a ray source of the gamma ray by back-tracing a trajectory of the secondary electron detected by the first and second radiation detectors; and
    (g) acquiring as an image data included in a reference energy range in which the sum of the energy of the secondary electron detected by the first to third radiation detectors.

10. The method of claim 9, wherein:
    step (b) includes measuring a position Pa1 and Pb1 where the plurality of secondary electrons passes through the first radiation detector and energy Ea1 and energy Eb1 transferred by the secondary electron at the time when the plurality of secondary electrons passes through the position Pa1 and the position Pb1, and
    step (c) includes measuring a position Pa2 and a position Pb2 where the secondary electron passing through the first radiation detector passes through the second radiation detector and energy Ea2 and energy Eb2 transferred by the secondary electron at the time when the secondary electron passes through the positions Pa2 and Pb2.

11. The method of claim 10, wherein:
    in step (f),
    a trajectory connecting the measured positions Pa1 and Pa2 and a trajectory connecting the positions Pb1 and Pb2 are back-projected to judge a point where both trajectories cross each other as the position of the ray source of the gamma ray.

12. The method of claim 11, wherein:
    in step (e),
    the data of the secondary electron simultaneously detected by the first to third radiation detectors is selected by using a coincidence circuit.

13. The method of claim 12, wherein:
    in step (e),
    the data included in a reference energy range in which the sum of the energy of the secondary electron detected by the first to third radiation detectors is selected.

14. The method of claim 13, wherein:
    in step (e),
    the data included in respective reference energy ranges in which the energy of the secondary electron transferred to the first and second radiation detectors are selected.

* * * * *